United States Patent [19]

Ward

[11] Patent Number: 4,788,202
[45] Date of Patent: Nov. 29, 1988

[54] SULPHONAMIDE DERIVATIVES AS $\alpha_2$-ADRENOCEPTOR ANTAGONISTS

[75] Inventor: Terence J. Ward, Maidenhead, England

[73] Assignee: John Wyeth & Brother Limited, Maidenhead, England

[21] Appl. No.: 71,504

[22] Filed: Jul. 9, 1987

Related U.S. Application Data

[63] Continuation-in-part of Ser. No. 893,421, Aug. 5, 1986, abandoned.

[30] Foreign Application Priority Data

Aug. 10, 1985 [GB] United Kingdom ............ 8520151
Mar. 11, 1986 [GB] United Kingdom ............ 8605923

[51] Int. Cl.[4] ............... A61K 31/435; C07D 471/14; C07D 491/147; C07D 495/14
[52] U.S. Cl. ........................ 514/285; 546/62; 546/70
[58] Field of Search ............ 546/62, 70; 514/285

[56] References Cited

U.S. PATENT DOCUMENTS 4,640,924 2/1987 White et al. ............ 514/291
4,686,226 8/1987 Huff et al. ............ 546/62
4,690,928 9/1987 Huff et al. ............ 546/62 X

FOREIGN PATENT DOCUMENTS 0154142 9/1985 European Pat. Off. .

Primary Examiner—Donald G. Daus
Assistant Examiner—William A. Teoli, Jr.
Attorney, Agent, or Firm—George Tarnowski

[57] ABSTRACT

The invention concerns sulphonamides of general formula

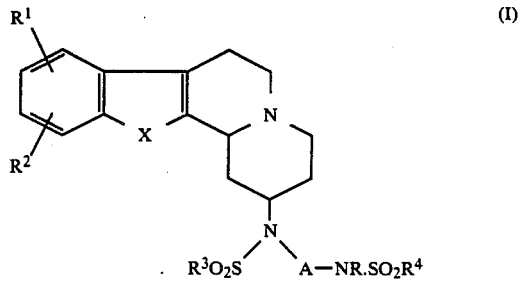

(I)

and their pharmaceutically acceptable acid addition salts. In formula (I), R represents hydrogen or lower alkyl, $R^1$ and $R^2$ which may be the same or different each represents hydrogen, lower alkyl, lower alkoxy or halogen, $R^3$ and $R^4$ which may be the same or different each represents lower alkyl, halo(lower)alkyl or aryl, A represents a lower alkylene group having 1 to 3 carbon atoms in the chain between the two N atoms and X represents O, S or $NR^5$ (where $R^5$ is hydrogen or lower alkyl). The compounds possess $\alpha_2$-adrenoceptor antagonistic activity in warm blooded animals.

7 Claims, No Drawings

SULPHONAMIDE DERIVATIVES AS α₂-ADRENOCEPTOR ANTAGONISTS

This application is a continuation-in-part of U.S. Ser. No: 893,421 filed Aug. 5, 1986, now abandoned.

The invention relates to sulphonamides, to processes for preparing the sulphonamides, to their use and to pharmaceutical compositions containing them.

GB No. 2136804A discloses various benzo[a]quinolizine sulphonamides that possess $\alpha_2$ antagonistic activity in warm blooded animals. The present invention provides certain novel benzo[b]furo-, indolo- and benzo[b]thienoquinolizinesulphonamides.

The novel compounds of the present invention are sulphonamides of the formula (I)

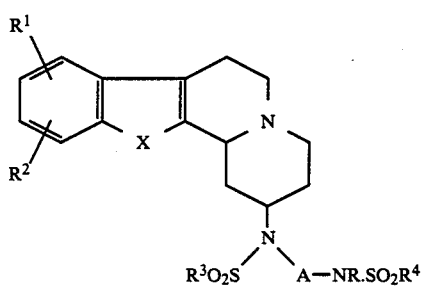

and their pharmaceutically acceptable acid addition salts. In formula (I), R represents hydrogen or lower alkyl, $R^1$ and $R^2$ which may be the same or different each represents hydrogen, lower alkyl, lower alkoxy or halogen, $R^3$ and $R^4$ which may be the same or different each represents lower alkyl, halo(lower)alkyl or aryl, A represents a lower alkylene group having 1 to 3 carbon atoms in the chain between the two N atoms and X represents O, S or $NR^5$(where $R^5$ is hydrogen or lower alkyl).

The term "lower" as used herein means that the radical referred to contains 1 to 6 carbon atoms. Preferably such radicals contain 1 to 4 carbon atoms. For example, a lower alkyl group may be methyl, ethyl, propyl or butyl. When $R^1$ and/or $R^2$ represents lower alkoxy the group may be, for example, methoxy, ethoxy, propoxy or butoxy. When $R^1$ and/or $R^2$ represents halogen the substituent may be, for example, fluorine, chlorine or bromine. Preferably both $R^1$ and $R^2$ are hydrogen.

The lower alkylene group A may be branched or straight chain provided that there are 1 to 3 carbon atoms in the chain between the two N atoms. For example, the lower alkylene group may be methylene, ethylene, trimethylene or a branched chain group such as ethylethylene or propylene [—CH(CH₃).CH₂—]. Preferably A is ethylene.

When a radical is referred to as "aryl" that radical is preferably a phenyl or substituted phenyl group. The substituted phenyl group can be a phenyl group substituted by one or more substituents chosen from, for example, halogen (e.g. chlorine, fluorine or bromine), alkoxy (e.g. lower alkoxy such as methoxy or ethoxy), lower alkyl (e.g. methyl, ethyl, propyl or butyl), alkylenedioxy (e.g. methylenedioxy or ethylenedioxy), nitro, amino, acylamino (particularly lower acylamino), lower alkylamino, diloweralkylamino or trifluoromethyl.

Examples of $R^3$ and $R^4$ are lower alkyl, such as methyl, ethyl, propyl or butyl, aryl such as phenyl or phenyl substituted by one or more of the substituents mentioned above and halo(lower)alkyl. The halo substituent in a halo(lower)alkyl group may be fluorine, chlorine, bromine or iodine. More than one halo atom may be present in the halo(lower)alkyl group; if more than one halo atom is present the halo atoms may be on the same carbon atom of the (lower)alkyl radical or on different carbon atoms (if the radical contains more than one carbon atom). Examples of halo(lower)alkyl groups include, for example, trifluoromethyl and chloromethyl.

Preferably $R^4$ is lower alkyl, e.g. methyl, and $R^3$ is lower alkyl (e.g. methyl or propyl) or phenyl.

Preferably R is hydrogen. Preferably $R^5$ is hydrgen or methyl.

The compounds of the invention in which $R^3$ and $R^4$ are the same may be prepared by reacting a reactive derivative of a sulphonic acid of formula $$R^6SO_2OH \qquad (II)$$

(where $R^6$ has the meanings of $R^3$ and $R^4$ above) with a quinolizine of the general formula

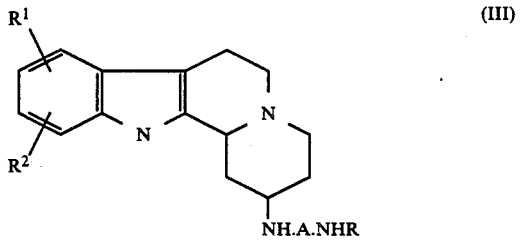

(wherein X,R,$R^1$,$R^2$ and A are as defined above) and, if required, converting a free base into a pharmaceutically acceptable acid addition salt. The reactive derivative of the sulphonic acid can be, for example, the acid halide or anhydride. Preferably it is the acid halide, i.e. a compound of formula $$R^6SO_2W \qquad (V)$$

(where $R^6$ is as defined above and W is halogen, preferably chlorine). The reaction is generally carried out under basic conditions.

The starting materials of general formula (III) are novel and may be prepared by reductive amination of a ketone of general formula

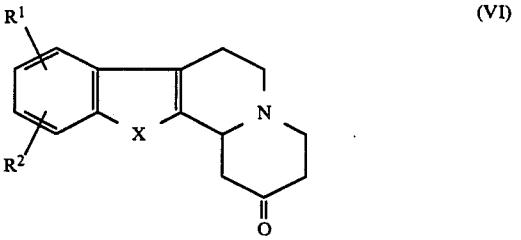

where X,$R^1$ and $R^2$ have the meanings given above. For example, the ketone may be reacted with a diamine of formula $$NH_2—A—NHR \qquad (VII)$$

(where A and R have the meanings given above) and with a hydride transfer agent, e.g. sodium borohydride.

The compounds of formula III are included in the invention.

Compounds of the invention in which $R^3$ and $R^4$ are the same or different may be prepared by other alternative methods. For example, a quinolizine of general formula (VIII)

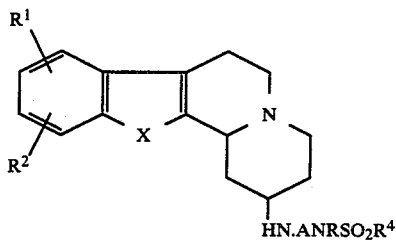

(VIII)

(wherein $X, A, R, R^1, R^2$ and $R^4$ have the meanings given above) may be reacted with a reactive derivative of the sulphonic acid of formula (II) above, in an analogous manner to that described above in connection with the reaction of the quinolizine (III). The quinolizine (VIII) is novel and may be prepared by known methods. For example, the quinolizine of formula (III) may be selectively sulphonated with the reactive derivative of the sulphonic acid (II) using the requisite amount of reactive derivative for forming the monosulphonamide (VIII) rather than the disulphonamide (I); it may be necessary to block one of the amine groups in the diamine (III) with a protecting group such as benzyl and remove the protecting group after the sulphonation. The quinolizine (VIII) alternatively may be prepared by reductive amination of the ketone (VI) with an amine $NH_2ANRSO_2R^4$ (where A, R and $R^4$ have the meanings given above) and a hydride transfer agent such as sodium borohydride.

Another method of preparing the compounds of the invention comprises reaction of a quinolizine of general formula

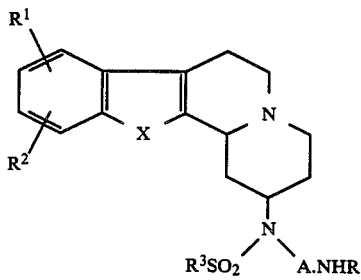

(IX)

(where $X,A,R,R^1,R^2$ and $R^3$ are as defined above) with a reactive derivative of the sulphonic acid of formula (II) in an analogous manner to that described above in connection with the reaction of the benzoquinolizine (III). The benzoquinolizine starting material of formula (IX) is novel and may be prepared by methods known per se. For example, a quinolizine of general formula

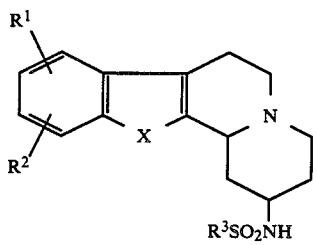

(X)

(where $X, R^1, R^2$ and $R^3$ have the meanings given above) may be reacted with an appropriate protected haloamine of formula Y-A-Q (where A has the meaning given above, Y is halogen and Q is a protected amino group), e.g. a phthalimido protected haloamine of formula

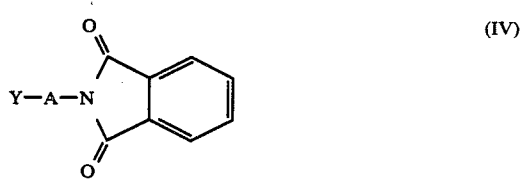

(IV)

(where A has the meaning given above and Y is halogen, preferably bromine) in presence of a strong base such as sodium hydride or lithium diisopropylamide and the protecting group removed. The compounds of general formula (X) may be prepared from the ketones of general formula (VI) by analogous methods known in the art.

Yet another method of preparing the compounds of the invention comprises reaction of a quinolizine of formula (X) above with a compound of formula $$W\text{-}A\text{-}NRSO_2R^4 \qquad (XI)$$

(where W,A,R and $R^4$ are as defined above) in presence of a strong base such as sodium hydride or lithium diisopropylamide.

Compounds of the invention in which R is lower alkyl may also be produced by alkylation of the compounds of the invention in which R is hydrogen. Compounds of the invention in which $R^3$ and/or $R^4$ is amino substituted phenyl may be prepared by reduction of compounds in which $R^3$ and/or $R^4$ is nitro substituted phenyl. Similarly compounds in which $R^3$ and/or $R^4$ is acylamino substituted phenyl may be prepared by acylation of compounds in which $R^3$ and/or $R^4$ is amino substituted phenyl.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compond.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess two asymmetric carbon atoms and hence can exist in various stereochemical forms. In addition they can exist as cis or trans isomers. It will be realised that if the starting material of formula (III) is a mixture of isomers the product of formula (I) will also be a mixture of isomers unless the mixture is separated by standard procedures. The preferred compounds of the invention are the trans isomers in which the $—N(SO_2R^3).A.NR.SO_2R^4$ group is in the equatorial position, i.e. compounds of the general formula (XII)

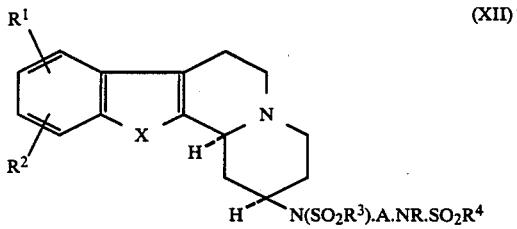

(XII)

and the pharmaceutically acceptable acid addition salts thereof. These compounds can be prepared by the methods described above from the corresponding trans isomer starting material.

The present invention also provides the novel intermediates of general formulae (III), (VIII) and (IX). Such compounds have the general formula (XIII)

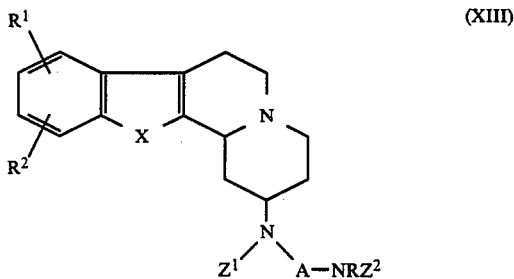

(XIII)

or acid addition salts thereof, wherein $R, R^1, R^2, X$ and $A$ are as defined above and $Z^1$ and $Z^2$ are both hydrogen or $Z^1$ is hydrogen and $Z^2$ is $SO_2R^4$ (where $R^4$ is as defined above) or $Z^1$ is $SO_2R^3$ (where $R^3$ is as defined above) and $Z^2$ is hydrogen.

The compounds of the present invention possess pharmacological activity. In particular the compounds possess $\alpha_2$-adrenoceptor antagonistic activity in warm blooded animals and hence are of value in conditions where antagonism of the $\alpha_2$-adrenoceptor is desirable, for example, as anti-depressants, in treatment of diabetes and in inhibiting blood platelet aggregation.

The compounds of the invention may be tested for $\alpha_2$-adrenoceptor antagonistic activity on the rat field stimulated vas deferens preparation using a modification of the method of Drew, Eur. J. Pharmac., 1977,42, 123–130 as described in our GB patent No. 2136804A Specification and for the $\alpha_1$-antagonist activity by the method based on that of Gillespie Br. J. Pharmac 1972, 45 404–416, as also described in GB patent specification No. 2136804A.

When tested for $\alpha_2$- and $\alpha_1$-adrenoceptor antagonist activity by the above mentioned procedures, N-[(2β, 12b α)-1,3,4,6,7,12b-hexahydro-2H-benzo [b] furo[2,3-a]quinolizin-2-yl]-N-(2-methanesulphonamidoethyl)methanesulphonamide, a representative compound of the invention has been found to have a pA$_2$ for $\alpha_2$-adrenoceptor antagonist activity of 8.07 and a pA$_2$ for $\alpha_1$-adrenoceptor antagonistic activity of 6.56; the $\alpha_2/\alpha_1$ selectivity [i.e. antilog of ($\alpha_2$ pA$_2$- $\alpha_1$ pA$_1$)] is 32 indicating that the compound shows great selectivity towards the $\alpha_2$-receptors.

The invention further provides a compound of formula (I) or a pharmaceutically acceptable acid addition salt for use in antagonising $\alpha_2$-adrenoceptors in a mammal.

The invention also provides a pharmaceutical composition comprising a compound of general formula (II) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (eg. hard and soft gelatin capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention:

EXAMPLE 1

N-[(2β,12bα)-1,3,4,6,7,12b-Hexahydro-2H-benzo[b]furo [2,3-a]--quinolizin-2-yl]ethylenediamine A mixture of 1,3,4,6,7,12bα-hexahydrobenzo[b]furo [2,3-a]quinolizin-2-one (0.82 g) and ethylenediamine (5 ml) in ethanol (25 ml) was heated to reflux under nitrogen for 3 hours. The reaction mixture was cooled in an ice bath and treated portionwise with sodium borohydride (0.5 g) and allowed to stir at room temperature overnight. The solvent was removed in vacuo and the residue was partitioned between water (50 ml) and chloroform (50 ml). The organic phase was separated, combined with two further chloroform washes (2×50 ml), washed with brine (10 ml), dried (Na₂SO₄), and concentrated in vacuo to leave a pale yellow oil. This was dissolved in methanol (50 ml) and acidified with ethanolic hydrogen chloride. The precipitated material was collected by filtration (0.97 g) and recrystallised from methanol to afford the title compound as the hydrochloride hydrate 0.75 g, a white solid, m.p. 200°–205° C.

EXAMPLE 2

N-[(2β,12bα)-1,3,4,6,7,12b-Hexahydro-2H-benzo[b]furo [2,3-a]quinolizin-2-yl]-N-(2-methanesulphonamidoethyl) methanesulphonamide A solution of methanesulphonyl chloride (407 mg) in dichloromethane (5 ml) was added dropwise over 1 min. to a stirred ice cooled mixture of the triamine trihydrochloride from Example 1 (638 mg) and triethylamine (883 mg) in dichloromethane (10 ml) and the mixture stirred at room temperature for 18 hours. The reaction mixture was filtered to remove a small amount of insoluble material and the filtrate was washed with saturated sodium bicarbonate solution (50 ml). The organic phase was combined with a chloroform wash (20 ml), dried (Na₂SO₄) and concentrated in vacuo to leave a white foam (0.70 g) which was recrystallised from methanol (50 ml) to afford the pure title base (0.45 g). The base (0.39 g) was suspended in ethanol (5 ml) and acidified with a solution of maleic acid (0.13 g) in ethanol (5 ml) to afford the title compound as the acid maleate (0.47 g), white prisms m.p.187°–189° C.

EXAMPLE 3

N-[(2β,12bα)-1,3,4,6,7,12b-Hexahydro-2H-benzo[b]furo [2,3-a]quinolizin-2-yl]-N-(2-ethanesulphonamidoethyl) ethanesulphonamide N-[(2β,12bα)-1,3,4,6,7,12b-hexahydro-2H-benzo[b]furo[2,3-a]quinolizin-2-yl]-ethylenediamine trihydrochloride (3 mmol) is basified with sodium hydroxide and extracted into CH₂Cl₂. The extract is dried and evaporated. The residue obtained above is dissolved in CH₂Cl₂ (20 cm³) and triethylamine (1.5 g) is added, followed by dropwise addition of ethanesulphonyl chloride (0.8 ml) to the stirred mixture. After stirring for a further 15 min. the solution is washed with aqueous sodium carbonate, dried and evaporated. The residue is crystallised from ethanol to give the title compound.

EXAMPLE 4

N-[-(2β,12bα)-1,3,4,6,7,12b-Hexahydro-2H-indolo[2,3-a]-quinolizin-2-yl]ethylenediamine 2-Oxo-1,3,4,6,7,12bα-hexahydro-2H-indolo[2,3-a]quinolizine hydrochloride (10 g) and ethylene diamine (10 ml) in ethanol (50 ml) is heated at reflux for 2 hours. The solution is then cooled in ice and sodium borohydride (1.5 g) added carefully with stirring. The mixture is then allowed to stir at ambient temperature overnight. The solution is evaporated, diluted with water and extracted into chloroform. The extract is dried and evaporated and the residue dissolved in ethanol (50 cm³) and acidified with ethanolic-HCl to precipitate the title compound as the crystalline trihydrochloride.

EXAMPLE 5

N-(2-[((2β,12bα)-1,3,4,6,7,12b-Hexahydro-2H-indolo[2,3-a]-quinolizin-2-yl)amino]ethyl)methanesulphonamide Methanesulphonic anhydride (11.3 g) is added portionwise over 2–3 min. to a vigorously stirred, ice cooled mixture of N-[-(2β,12bα)-1,3,4,6,7,12b-hexahydro2H-indolo[2,3-a]quinolizin-2-yl]ethylenediamine trihydrochloride (0.05 mol), potassium carbonate (27.6 g), CH₂Cl₂ (200 cm³) and water (100 cm³). After stirring for a further 0.5 hour the mixture is diluted with water, to dissolve MeSO₃K, the organic phase is separated and the aqueous phase extracted with chloroform. The combined organic phases are dried and evaporated. The residue is dissolved in ethanol:methanol and acidified with aqueous hydrobromic acid (60% w/v) to precipitate title compound as the dihydrobromide on ice cooling.

EXAMPLE 6

N-[(2β,12bα)-1,3,4,6,7,12b-Hexahydro-2H-indolo[2,3-a]-quinolizin-2-yl]-N-(2-methanesulphonamido)ethyl)-ethanesulphonamide Ethanesulphonyl chloride (1.0 ml) is added dropwise to a stirred, ice cooled mixture of N-(2-[((2β, 12bα)-1,3,4,6,7,12b-hexahydro-2H-indolo[2,3-a]quinolizin-2-yl)amino]ethyl)methanesulphonamide (5 mmol, prepared from the dihydrobromide), triethylamine (1.25 g) and dichloromethane (15 ml). After addition is complete the solution is stirred at ambient temperature for 1 hour, washed with sodium carbonate solution, dried and evaporated. The residue is chromatographed on neutral alumina to give the title compound as the free base. The base is dissolved in ethanol (15 ml) and acidified with maleic acid to precipitate the maleate.

EXAMPLE 7

N-[(2β,12bα)-1,3,4,6,7,12b-Hexahydro-2H-indolo[2,3-a]-quinolizin-2-yl]-N-(2-ethanesulphonamidoethyl)ethanesulphonamide Ethanesulphonyl chloride (2.7 g) is added over about 5 min. to a stirred ice cooled mixture of N-((-2β,12bα)-1,3,4,6,7,12b-hexahydro-2H-indolo[2,3-a]quinolizin-2-yl)ethylenediamine (10 mmol, prepared from the trihydrochloride), triethylamine (2.5 ml) and dichloromethane (25 ml). After addition is complete, the reaction is stirred at ambient temperature for 1 hour, washed with sodium, carbonate solution, dried and evaporated. The residue is dissolved in ethanol (30 ml) and acidified with maleic acid to precipitate the title compound as the maleate.

EXAMPLE 8

N-(2-[((2β,12bα)-1,3,4,6,7,12b-Hexahydro-2H-benzo[b-]furo [2,3-a]-quinolizin-2-yl)amino]ethyl)methanesulphonamide Methanesulphonic anhydride (17 g) is added portionwise over 2-3 min. to a vigorously stirred ice cooled mixture of N-[(2β,11bα)-1,3,4,6,7,12b-hexahydro-2H-benzo[b]furo[2,3-a]quinolizin-2-yl]ethylenediamine trihydrochloride (30.9 g), potassium carbonate (41.4 g), CH$_2$Cl$_2$ (300 cm$^3$) and water (150 cm$^3$). After stirring for a further 0.5 hour the organic phase is separated, dried and evaporated. The residual oil is dissolved in ethanol and acidified with aqueous hydrobromic acid (60% w/v) to give the title dihydrobromide.

EXAMPLE 9

N-[(2β,12bα)-1,3,4,6,7,12b-Hexahydro-2H-benzo[b-]furo [2,3-a]-quinolizin-2-yl]-N-(2-methanesulphonamido-ethyl) benzenesulphonamide Benzenesulphonyl chloride (0.93 g, 0.67 ml) is added to a stirred ice-cooled mixture of N-(2-[((2β,12bα)-1,3,4,6,7,12b-hexahydro-2H-benzo[b]furo[2,3-a]quinolizin-2-yl)amino]ethylmethanesulphonamide (5 mmol, prepared from the dihydrobromide), triethylamine (1.25 g) and CH$_2$Cl$_2$ (20 ml). The mixture is then stirred for 1 hour, washed with sodium carbonate solution, dried and evaporated. The residue is dissolved in ethanol and acidified with ethanolic hydrogen chloride to give the title hydrochloride.

EXAMPLE 10

N-[(2β,12bα)-1,3,4,6,7,12b-Hexahydro-2H-benzo[b-]furo [2,3-a]quinolizin-2-yl]-N-(2-methanesulphonamidoethyl)-p-methylbenzenesulphonamide The procedure of Example 9 is followed using p-methylbenzenesulphonyl chloride in place of benzenesulphonyl chloride to give the title compound hydrochloride. chloride.

EXAMPLE 11

N-[(2β,12bα)-1,3,4,6,7,12b-Hexahydro-2H-benzo[b]-thieno [2,3-a]quinolizin-2-yl]ethylenediamine A mixture of 1,3,4,5,7,12bα-hexahydrobenzo[b]-thieno [2,3-a]quinolizin-2-one hydrochloride (5 g) and ethylene diamine (5 ml) in ethanol (25 ml) is heated at reflux for 2 hours. The solution is then cooled in ice and sodium borahydride (0.8 g) added carefully with stirring. The mixture is stirred for a further 16 hours then evaporated. The residue is diluted with water and extracted with chloroform. The extract is dried and evaporated, the residue dissolved in ethanol and acidified with ethanolic hydrogen chloride to give the title trihydrochloride.

EXAMPLE 12

N-[(2β,12bα)-1,3,4,6,7,12b-Hexahydro-2H-benzo[b]-thieno 2,3-a]quinolizin-2-yl]-N-(2-methanesulphonamidoethyl) methanesulphonamide The procedure of Example 2 is followed using N-[(2β,12bα)-1,3,4,6,7,12b-hexahydrobenzo[b]thieno[2,3-a]quinolizin-2-yl]ethylenediamine trihydrochloride (in place of the benzo[b]furo[2,3-a]quinolizinyl-ethylenediamine trihydrochloride) to give the title compound acid maleate.

I claim:

1. A compound selected from the group consisting of a sulphonamide of the formula (I)

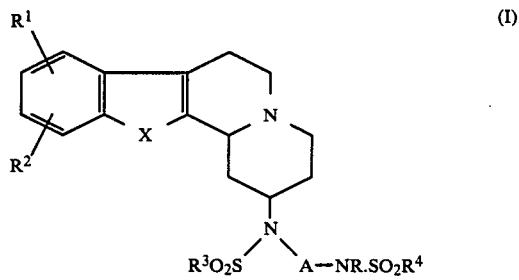

and a pharmaceutically acceptable acid addition salt thereof, wherein R represents hydrogen or lower alkyl, R$^1$ and R$^2$ which may be the same or different each represents hydrogen, lower alkyl, lower alkoxy or halogen, R$^3$ and R$^4$ which may be the same or different each represents lower alkyl, halo(lower)alkyl or phenyl or pheny substituted by one or more substituents selected from halogen, lower alkoxy, lower alkyl, alkylenedioxy, nitro, amino, lower acylamino, lower alkylamino, diloweralkylamino and trifluoromethyl, A represents a lower alkylene group having 1 to 3 carbon atoms in the chain between the two N atoms and X represents O, S or NR$^5$ (where R$^5$ is hydrogen or lower alkyl).

2. A compound as claimed in claim 1 wherein A is ethylene.

3. A compound according to claim 1 which is N-[(2β, 12bα)-1,3,4,6,7,12b-hexahydro-2H-benzo[b]furo[2,3-a]quinolizin-2-yl]-N-(2-methanesulphonamidoethyl)methanesulphonamide or a pharmaceutically acceptable acid addition salt thereof.

4. A compound according to claim 1 which is N-[(2β,12bα)-1,3,4,6,7,12b-hexahydro-2H-benzo[b-]furo[2,3-a]quinolizin-2-yl]-N-(-2-ethanesulphonamidoethyl)ethanesulphonamide, or N-[(2β,12bα)-1,3,4,6,7,12b-hexahydro-2H-indolo[2,3-a]quinolizin-2-yl]-N-(2-methanesulphonamido)ethyl)ethanesulphonamide, or N-[(2β,12bα)-1,3,4,6,7,12b-hexahydro-2H-indolo[2,3-a]quinolizin-2-yl]-N(-2-ethanesulphonamidoethyl)ethanesulphonamide, or N-[(2β,12bα)-1,3,4,6,7,12b-hexahydro-2H-benzo[b]furo [2,3-a]quinolizin-2-yl]-N-(2-methanesulphonamidoethyl)benzenesulphonamide, or N-[(2β,12bα)-1,3,4,6,7,12b-hexahydro-2H-benzo[b]furo[2,3-a]quinolizin-2-yl]-N-(2-methanesulphonamidoethyl)-p-methylbenzenesulphonamide, or N-[(2β,12bα)-1,3,4,6,7,12b-hexahydro-2H-benzo[b]thieno[2,3-a]-quinolizin-2-yl]-N-(2-methanesulphonamidoethyl)methanesulphonamide or a pharmaceutically acceptable acid addition salt thereof.

5. A pharmaceutical composition having α₂-adrenoceptor antagonistic activity comprising an amount effective to antagonise α₂-adrenoceptors of a compound selected from the group consisting of a sulphonamide of the formula (I)

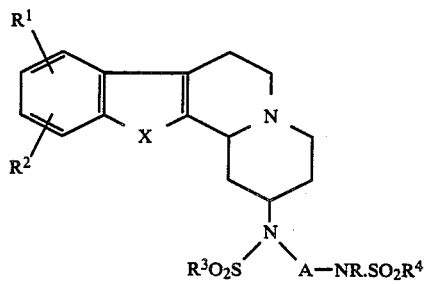

and a pharmaceutically acceptable acid addition salt thereof, wherein R represents hydrogen or lower alkyl, $R^1$ and $R^2$ which may be the same or different each represents hydrogen, lower alkyl, lower alkoxy or halogen, $R^3$ and $R^4$ which may be the same or different each represents lower alkyl, halo(lower)alkyl or phenyl or phenyl substituted by one or more substituents selected from halogen, lower alkoxy, lower alkyl, alkylenedioxy, nitro, amino, lower acylamino, lower alkylamino, diloweralkylamino and trifluoromethyl, A represents a lower alkylene group having 1 to 3 carbon atoms in the chain between the two N atoms and X represents O, S or $NR^5$ (where $R^5$ is hydrogen or lower alkyl) and a pharmaceutically acceptable carrier.

6. A method of antagonising α₂-adrenoceptors in warm blooded animals which comprises administering to the animal an effective amount of a compound selected from the group consisting of a sulphonamide of the formula (I)

(I)

and a pharmaceutically acceptable acid addition salt thereof, wherein R represents hydrogen or lower alkyl, $R^1$ and $R^2$ which may be the same or different each represents hydrogen, lower alkyl, lower alkoxy or halogen, $R^3$ and $R^4$ which may be the same or different each represents lower alkyl, halo(lower)alkyl or phenyl or phenyl substituted by one or more substituents selected from halogen, lower alkoxy, lower alkyl, alkylenedioxy, nitro, amino, lower acylamino, lower alkylamino, diloweralkylamino and trifluoromethyl, A represents a lower alkylene group having 1 to 3 carbon atoms in the chain between the two N atoms and X represents O, S or $NR^5$ (where $R^5$ is hydrogen or lower alkyl).

7. A compound of formula (XIII)

(XIII)

or an acid addition salt thereof, wherein R, $R^1$, $R^2$, X and A are as defined in claim 1 and $Z^1$ and $Z^2$ are both hydrogen or $Z^1$ is hydrogen and $Z^2$ is $SO_2R^4$ (where $R^4$ is as defined in claim 1) or $Z^1$ is $SO_2R^3$ (where $R^3$ is as defined in claim 1) and $Z^2$ is hydrogen.

* * * * *